(12) United States Patent
Kameyama et al.

(10) Patent No.: US 11,426,347 B2
(45) Date of Patent: *Aug. 30, 2022

(54) FOOD FOR IMPROVING INTRAINTESTINAL ENVIRONMENT

(71) Applicant: AJINOMOTO CO., INC., Tokyo (JP)

(72) Inventors: Keishi Kameyama, Kanagawa (JP); Momoka Tsuneyoshi, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 184 days.

This patent is subject to a terminal disclaimer.

(21) Appl. No.: 16/579,135

(22) Filed: Sep. 23, 2019

(65) Prior Publication Data

US 2020/0009046 A1 Jan. 9, 2020

Related U.S. Application Data

(63) Continuation of application No. PCT/JP2018/013052, filed on Mar. 28, 2018.

(30) Foreign Application Priority Data

Mar. 28, 2017 (JP) .............................. JP2017-063145

(51) Int. Cl.
| | |
|---|---|
| *A23K 20/142* | (2016.01) |
| *A23K 20/163* | (2016.01) |
| *A23K 50/10* | (2016.01) |
| *A23K 50/30* | (2016.01) |
| *A23L 33/175* | (2016.01) |
| *A61K 31/197* | (2006.01) |
| *A61K 31/198* | (2006.01) |
| *A61K 31/401* | (2006.01) |
| *A61K 31/702* | (2006.01) |
| *A61K 47/38* | (2006.01) |
| *A61P 1/14* | (2006.01) |
| *A61K 9/00* | (2006.01) |
| *A23K 50/60* | (2016.01) |
| *A23L 33/26* | (2016.01) |
| *A61K 31/4172* | (2006.01) |
| *A61K 9/48* | (2006.01) |
| *A61K 31/195* | (2006.01) |

(52) U.S. Cl.
CPC .......... *A61K 9/0056* (2013.01); *A23K 20/142* (2016.05); *A23K 20/163* (2016.05); *A23K 50/10* (2016.05); *A23K 50/30* (2016.05); *A23K 50/60* (2016.05); *A23L 33/175* (2016.08); *A23L 33/26* (2016.08); *A61K 9/0053* (2013.01); *A61K 9/4816* (2013.01); *A61K 31/195* (2013.01); *A61K 31/197* (2013.01); *A61K 31/198* (2013.01); *A61K 31/401* (2013.01); *A61K 31/4172* (2013.01); *A61K 31/702* (2013.01); *A61K 47/38* (2013.01); *A61P 1/14* (2018.01); *A23V 2002/00* (2013.01)

(58) Field of Classification Search
CPC .. A61K 9/0056; A61K 31/197; A61K 31/198; A61K 31/702; A61K 31/4172; A61K 31/401; A61K 47/38; A23L 33/175; A23L 33/26; A23K 50/30; A23K 50/60; A23K 50/10; A23K 20/142; A23K 20/163; A61P 1/14; A23V 2002/00

USPC .......................................................... 514/61

See application file for complete search history.

(56) References Cited

U.S. PATENT DOCUMENTS

| | | |
|---|---|---|
| 2007/0009502 A1 | 1/2007 | Lall et al. |
| 2012/0121621 A1 | 5/2012 | Jaszberenyi et al. |
| 2015/0297546 A1 | 10/2015 | Morita et al. |
| 2015/0329648 A1 | 11/2015 | Nagahata et al. |
| 2016/0022592 A1 | 1/2016 | Kabadi et al. |
| 2016/0039944 A1 | 2/2016 | Shinkura |
| 2020/0009167 A1 | 1/2020 | Kameyama et al. |

FOREIGN PATENT DOCUMENTS

| | | | |
|---|---|---|---|
| CN | 104286542 | * | 1/2015 |
| CN | 104286542 A | | 1/2015 |
| JP | 2000-245393 A | | 9/2000 |
| JP | 2002-226369 A | | 8/2002 |
| JP | 2009-517032 A | | 4/2009 |
| JP | 2016-047057 A | | 4/2016 |
| WO | WO03/009704 A2 | | 2/2003 |
| WO | WO2005/055737 A1 | | 6/2005 |
| WO | WO2006/127424 A2 | | 11/2006 |
| WO | 2007/061860 A1 | | 5/2007 |
| WO | WO2009/054360 A1 | | 4/2009 |
| WO | WO2010/098822 A1 | | 9/2010 |
| WO | WO2013/168803 A1 | | 11/2013 |

(Continued)

OTHER PUBLICATIONS

Modesto et al. A novel strategy to select Bifidobacterium strains and prebiotics as natural growth promoters in newly weaned pigs. Livestock Science 122 (2009) 248-258. (Year: 2009).*

(Continued)

*Primary Examiner* — Yih-Horng Shiao
(74) *Attorney, Agent, or Firm* — Cermak Nakajima & McGowan LLP; Shelly Guest Cermak

(57) ABSTRACT

A food for improving intestinal environment by promoting proliferation of intestinal bifidobacteria is described herein. The food for improving intestinal environment can contain a combination of (1) an enteric composition containing an amino acid or a salt thereof and (2) an indigestible polysaccharide or a composition containing an indigestible polysaccharide.

7 Claims, 5 Drawing Sheets

Specification includes a Sequence Listing.

(56) References Cited

FOREIGN PATENT DOCUMENTS

| WO | WO2015/137387 A1 | 9/2015 |
| WO | WO2016/172658 A2 | 10/2016 |

OTHER PUBLICATIONS

Mitsuoka, T., "Bifidobacteria Research," Center for Academic Publications Japan, 1998, P70 with a partial English language translation thereof.

Gibson, G. R., et al., "Selective Stimulation of Bifidobacteria in the Human Colon by Oligofructose and Inulin," Gastroenterol. 1995;108:975-982.

Kolida, S., et al., "Prebiotic effects of inulin and oligofructose," Br. J. Nutr. 2002;87(Suppl. 2):S193-S197.

International Search Report and Written Opinion for PCT Patent App. No. PCT/JP2018/013052 (dated Jun. 26, 2018) with English translation of the ISR.

Extended European Search Report from European Patent App. No. 18777450.0 (dated Jan. 19, 2021).

International Search Report and Written Opinion for PCT Patent App. No. PCT/JP2018/013054 (dated Jun. 26, 2018) with English translation of the ISR.

Modesto., M., et al., "A novel strategy to select Bifidobacterium strains and prebiotics as natural growth promoters in newly weaned pigs," Livestock Sci. 2009;122:248-258.

Office Action from U.S. Appl. No. 16/579,191 dated May 24, 2021.

Extended European Search Report for European Patent App. No. 18777193.6 (dated Mar. 17, 2021).

Nutrition Boutique website "HMF Neuro Powder Probiotics 60g," (2011) 2 pp.; retrieved from the internet on Jul. 30, 2015.

* cited by examiner

SEQUENCE LISTING

<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: primer

<400> SEQUENCE: 1
ctcctggaaa cgggtgg                                                17

<210> SEQ ID NO 2

```
<211> LENGTH: 22
<212> TYPE: DNA
<213> ORGANISM: Artificial Sequence
<220> FEATURE:
<223> OTHER INFORMATION: primer

<400> SEQUENCE: 2
ggtgttcttc ccgatatcta ca                                                    22
```

FOOD FOR IMPROVING INTRAINTESTINAL ENVIRONMENT

This application is a Continuation of, and claims priority under 35 U.S.C. § 120 to, International Application No. PCT/JP2018/013052, filed Mar. 28, 2018, and claims priority therethrough under 35 U.S.C. § 119 to Japanese Patent Application No. 2017-063145, filed Mar. 28, 2017, the entireties of which are incorporated by reference herein. Also, the Sequence Listing filed electronically herewith is hereby incorporated by reference (File name: 2019-09-23T_US-599_Seq_List; File size: 1 KB; Date recorded: Sep. 23, 2019).

BACKGROUND

Technical Field

The present invention relates to food for improving intestinal environment by promoting proliferation of intestinal bifidobacteria.

Review of Related Art

It is important for prevention of various diseases and promotion and maintenance of health to promote proliferation of beneficial bacteria such as intestinal bifidobacteria and the like and improve the intestinal environment via the normalization of intestinal bacterial flora.

National Publication of International Patent Application No. 2009-517032 discloses a sweetener composition containing prebiotics and describes that the prebiotics include mucopolysaccharides, oligosaccharides, polysaccharides, amino acids, vitamins, nutrient precursors, proteins, and combinations of these. However, the document does not show an experimental example demonstrating that the above-mentioned prebiotics cause proliferation of bifidobacteria in the gastrointestinal tract.

"Bifidobacteria Research" Tomotari MITSUOKA, (Center for Academic Publications Japan, 1998, P70) reports on the amino acid requirements of bifidobacteria. However, this report shows experimental results of a pure culture strain using a medium that is richer in nutrients than in the intestine, but does not show a complex system such as the lower gastrointestinal tract, or that the strain can be oligotrophic, and intestinal bacterial flora.

It is known that polysaccharides such as oligosaccharides and water-soluble dietary fibers such as inulin are difficult to digest and be absorbed in the stomach and small intestine, and therefore, reach the large intestine to become bait for beneficial bacteria such as bifidobacteria and the like (e.g., GIBSON et al., GASTROENTEROLOGY, Vol. 108, No. 4, pages 975-982, 1995; Kolida et al., Br J Nutr. 2002 May; 87 Suppl 2: S193-197).

SUMMARY

It is an aspect of the present invention to provide a food for improving the intestinal environment by promoting proliferation of intestinal bifidobacteria.

The Experimental Examples 1-1, 1-2 and 2, that is, the culture test using human feces suspension, and Experimental Example 3, that is, the administration test on pigs, demonstrate a remarkably superior promoting effect on the proliferation of bifidobacteria by supplying a combination of oligosaccharides or indigestible polysaccharides, and amino acids as an active ingredient as compared to when each is used singly.

In addition, amino acids are generally absorbed in the jejunum and upper ileum, and hence do not typically pass through to the lower gastrointestinal tract where bifidobacteria live. However, it is described herein that oligosaccharides or indigestible polysaccharides and amino acids can be simultaneously present in the lower gastrointestinal tract by forming an enteric composition of the amino acid.

It is an aspect of the present invention to provide a food for improving an intestinal environment comprising: (1) an enteric composition comprising an amino acid or a salt thereof, and (2) an indigestible polysaccharide or a composition comprising an indigestible polysaccharide.

It is a further aspect of the present invention to provide the food as described above, wherein the indigestible polysaccharide is an oligosaccharide.

It is a further aspect of the present invention to provide the food as described above, wherein the amino acid is selected from the group consisting of alanine, glutamine, glutamic acid, isoleucine, histidine, lysine, proline, valine, and combinations thereof.

It is a further aspect of the present invention to provide the food as described above, wherein the amino acid is selected from the group consisting of alanine, glutamine, glutamic acid, isoleucine, lysine, valine, and combinations thereof.

It is a further aspect of the present invention to provide the food as described above, wherein the amino acid is selected from the group consisting of glutamic acid, lysine, and a combination thereof.

It is a further aspect of the present invention to provide the food as described above, wherein the form of the enteric composition is selected from the group consisting of a granule, a granulated substance, a tablet, a hard capsule, and a soft capsule.

It is a further aspect of the present invention to provide the food as described above, wherein the form of the composition comprising an oligosaccharide is a drink.

It is a further aspect of the present invention to provide a commercial package comprising the food as described above, and written matter describing and explaining a method for improving the intestinal environment using said food.

It is a further aspect of the present invention to provide a food with an indication that it can be used for improving intestinal environment, comprising the food as described herein.

It is a further aspect of the present invention to provide a food for enhancing an intestinal environment improving effect comprising the food as described above.

It is a further aspect of the present invention to provide a food for enhancing an intestinal environment improving effect of an indigestible polysaccharide or a composition comprising an indigestible polysaccharide, said food being an enteric composition comprising an amino acid or a salt thereof.

It is a further aspect of the present invention to provide the food as described herein, said food being used for improving intestinal environment.

It is a further aspect of the present invention to provide a method for improving intestinal environment in a human comprising ingestion by the human of an effective amount of a food comprising (1) an enteric composition comprising an amino acid or a salt thereof, and (2) an indigestible polysaccharide or a composition comprising an indigestible polysaccharide.

It is a further aspect of the present invention to provide a method of producing a food for improving the intestinal environment comprising combining (1) an enteric composition comprising an amino acid or a salt thereof, and (2) an indigestible polysaccharide or a composition comprising an indigestible polysaccharide.

It is a further aspect of the present invention to provide a food for improving intestinal environment comprising: (1) an enteric composition comprising an amino acid, and (2) an oligosaccharide or a composition comprising an oligosaccharide.

It is a further aspect of the present invention to provide the food as described above, wherein the amino acid is selected from the group consisting of alanine, glutamine, glutamic acid, isoleucine, lysine, valine, and combinations thereof.

It is a further aspect of the present invention to provide the food as described above, wherein the amino acid is selected from the group consisting of glutamic acid, lysine, and a combination thereof.

It is a further aspect of the present invention to provide the food as described above, wherein the form of the enteric composition is selected from the group consisting of a granule, a tablet, a hard capsule, and a soft capsule.

It is a further aspect of the present invention to provide the food as described above, wherein the composition comprising an oligosaccharide is a drink.

It is a further aspect of the present invention to provide a commercial package comprising a food comprising (1) an enteric composition comprising an amino acid, and (2) an oligosaccharide or a composition comprising an oligosaccharide, and written matter describing and explaining a method for improving the intestinal environment using the food.

It is a further aspect of the present invention to provide a food with an indication that it can be used for improving an intestinal environment, comprising (1) an enteric composition comprising an amino acid and (2) an oligosaccharide or a composition comprising an oligosaccharide.

It is a further aspect of the present invention to provide a food for enhancing an intestinal environment improving effect comprising (1) an enteric composition comprising an amino acid, and (2) an oligosaccharide or a composition comprising an oligosaccharide.

It is a further aspect of the present invention to provide a food for enhancing an intestinal environment improving effect of a composition comprising an oligosaccharide or a composition comprising an oligosaccharide, said food being an enteric composition comprising an amino acid.

As described herein, a food having a remarkably superior promoting effect on the proliferation of bifidobacteria as compared to when each is used singly and a function to improve the intestinal environment can be provided by supplying a combination of an indigestible polysaccharide, such as an oligosaccharide or water-soluble dietary fiber, and an amino acid or a salt thereof.

As described herein, by supplying a combination of an amino acid or a salt thereof as an enteric composition and an indigestible polysaccharide, such as an oligosaccharide or water-soluble dietary fiber, the indigestible polysaccharide and the amino acid or a salt thereof can be simultaneously present in the lower gastrointestinal tract where bifidobacteria live, and proliferation of intestinal bifidobacteria can be promoted.

BRIEF DESCRIPTION OF THE DRAWINGS

FIG. 1-2 shows the results of Experimental Example 1-2.
FIG. 2 shows the results of Experimental Example 2.

DETAILED DESCRIPTION

Figure 1:
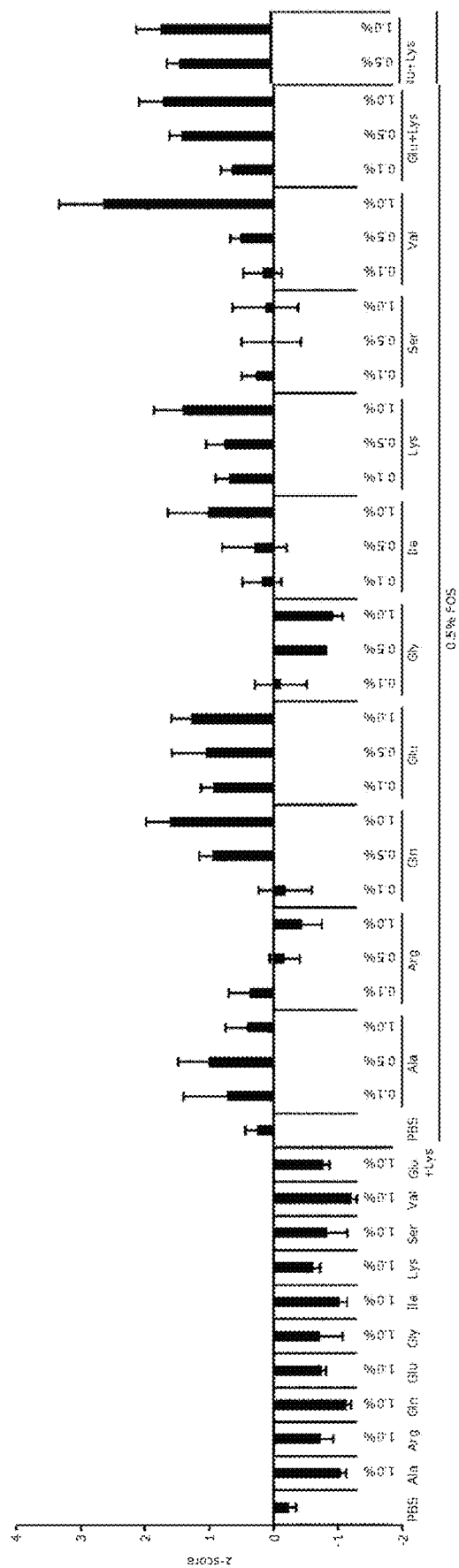
FIG. 1-1 shows the results of Experimental Example 1-1.

The food for improving intestinal environment as described herein is composed of a combination of (1) an enteric composition containing an amino acid or a salt thereof, and (2) an indigestible polysaccharide or a composition containing an indigestible polysaccharide.

The food is a combined-use food of (1) and (2) in which (1) and (2) are used in combination.

In the food as described herein, (1) and (2) may be simultaneously formulated and contained in the same preparation (food), or (1) and (2) may be formulated separately and ingested simultaneously or at different times by the same route or different routes. That is, the food as described herein includes a food containing (1) and (2) in one preparation, and a food combining (1) and (2) formulated separately.

The food as described herein is a concept that broadly encompasses foods that can be taken orally, excluding pharmaceuticals, and includes not only so-called "food" but also includes drinks, health supplements, foods with health claims, such as foods for specified health uses or foods with functional claims, supplements, and the like.

The phrase "improvement of intestinal environment" can refer to increasing the relative bifidobacteria present in the lower gastrointestinal tract. To relatively increase can mean to promote the predominance of bifidobacteria in the intestinal bacterial flora. The predominance of bifidobacteria in the intestinal bacterial flora can be confirmed by measuring the amount of bifidobacteria in feces by quantitative PCR or the like.

The "lower gastrointestinal tract" can mean the ileum, cecum, colon, and rectum.

Enteric Composition Containing an Amino Acid or a Salt Thereof

Examples of the amino acid include alanine, arginine, asparagine, cysteine, glutamine, glutamic acid, glycine, histidine, isoleucine, leucine, lysine, methionine, phenylalanine, proline, serine, threonine, and valine; and alanine, glutamine, glutamic acid, isoleucine, histidine, lysine, proline, and valine are particular examples. These amino acids can be in an L form. One or more of these amino acids can be used in combination.

As the amino acid, L-alanine, L-glutamine, L-glutamic acid, L-isoleucine, L-histidine, L-lysine, L-proline, L-valine, or a combination of these, such as a combination of L-glutamic acid and L-lysine is a particular example, and L-glutamic acid, L-lysine, or a combination of L-glutamic acid and L-lysine is another particular example.

The amino acid may be in the form of a salt. Examples include salts acceptable as medicament or food. Examples include alkali metal salts such as sodium salt, potassium salt and the like; alkaline earth metal salts such as calcium salt, magnesium salt, barium salt, and the like; aluminum salt; salts with organic bases such as ethylenediamine, propylenediamine, ethanolamine, monoalkylethanolamine, dialkylethanolamine, diethanolamine, triethanolamine, and the like; salts with inorganic acids such as hydrochloric acid, hydrobromic acid, nitric acid, sulfuric acid, phosphoric acid, and the like; and salts with organic acids such as formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, and the like; and sodium salt, potassium salt, or hydrochloride are particular examples.

The enteric composition is a composition that does not disintegrate in the stomach or the upper part of the small intestine where the pH is low, but disintegrates in the lower part of the small intestine or large intestine where the pH is high, and the amino acid or a salt thereof can be effective.

The enteric composition can disintegrate at pH 4 or more, pH 4-pH 9, or pH 5-pH 9.

The disintegration property can be measured, for example, according to the rules for enteric preparations in the disintegration test method, the Japanese Pharmacopoeia 17th edition.

Examples of the form of the enteric composition include granules including fine granules, a granulated substance, tablet, hard capsule, and soft capsule.

The enteric composition can be produced by a method known in the field of food preparation or pharmaceutical preparation.

For example, methods of production can include mixing, granulating and/or tableting an amino acid or a salt thereof together with a carrier, such as excipient, binder, disintegrant, lubricant, protector, to give a granule or tablet, then applying an enteric coating to the granule or tablet to give an enteric granule or enteric tablet; filling granules or tablets containing an amino acid or a salt thereof in a hard capsule applied with an enteric coating to give an enteric capsule; and encapsulating a suspension of an amino acid or a salt thereof in a carrier, such as an oil component, in a soft capsule composed of an enteric substrate to give an enteric capsule. In addition, the above-described enteric granules may be encapsulated in a capsule, such as a cellulose capsule, to give a capsule. Also, a molten mixture of oil and fat (protector) and an amino acid or a salt thereof may be solidified by cooling to give an enteric granulated substance.

Commercially available products can also be used.

Examples of the enteric coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L, methacrylic acid copolymer LD, methacrylic acid copolymer S, and the like; and naturally occurring substances such as shellac and the like. A coating additive such as a plasticizer may also be used during coating.

The carrier, coating base, and coating additive are used in amounts conventionally employed in the technical field of preparation formulation.

(2) Indigestible Polysaccharide or Composition Containing Indigestible Polysaccharide The indigestible polysaccharide is a polysaccharide that is not easily digested or absorbed in the stomach or small intestine, and that reaches the large intestine to be utilized by bifidobacteria.

The degree of polymerization of the indigestible polysaccharides is not less than 2 or not less than 3. The upper limit of the degree of polymerization of indigestible polysaccharides is not particularly limited and can be, for example, not more than 100, not more than 60, not more than 10, not more than 6, or not more than 5.

The degree of polymerization of the indigestible polysaccharides can be 2-100, 2-60, 2-10, or 2-6.

Examples of the indigestible polysaccharides include oligosaccharides, water-soluble dietary fiber, and the like.

Indigestible polysaccharides, such as oligosaccharides or water-soluble dietary fiber, can be used as they are, or can be in a composition containing indigestible polysaccharides, such as oligosaccharides or water-soluble dietary fiber.

The oligosaccharide can have 2 to 10 monosaccharides bonded thereto.

Examples of the oligosaccharide include coffee bean manno-oligosaccharide, lactosucrose oligosaccharide, galacto-oligosaccharide, fructo-oligosaccharide, soybean oligosaccharide, xylo-oligosaccharide, and isomalto-oligosaccharide; and fructo-oligosaccharide or galacto-oligosaccharide are particular examples. One or more kinds of oligosaccharides can be used in combination.

The oligosaccharide can be produced by a known method, and commercially available products can also be used.

Examples of the fructo-oligosaccharide include fructo-oligosaccharides with polymerization degree of 3-5 in which 1 to 3 fructoses are bonded to sucrose. Specifically, for example, FOS: Wako Pure Chemical Industries, Ltd., #064-02385 is a particular example.

Examples of the galacto-oligosaccharide include galacto-oligosaccharide with polymerization degree of 2-6 in which galactose is bonded to lactose. Specifically, for example, GOS: Wako Pure Chemical Industries, Ltd., #076-05945 is a particular example.

Water-soluble dietary fiber is a dietary fiber that is not easily digested or absorbed in the stomach or small intestine, and can reach the large intestine to be degraded by intestinal bacteria and utilized by bifidobacteria.

Examples of the water-soluble dietary fiber include inulin.

The water-soluble dietary fiber such as inulin can be produced by a known method, and commercially available products can also be used.

Inulin generally has a structure in which 2-60 molecules of fructose are polymerized by a $\beta(2\text{-}1)$ bond and a glucose molecule is bonded to the terminal.

Inulin is degraded by intestinal bacteria in the large intestine (partial hydrolysis) to fructo-oligosaccharide. Thus, an effect similar to the effect of fructo-oligosaccharide was confirmed in the Experimental Examples 1-1, 1-2, and is expected to be present in the gastrointestinal tract.

The form of the composition containing indigestible polysaccharides such as an oligosaccharide or water-soluble dietary fiber is not particularly limited and may be, for example, a powder, granule (including fine granules), tablet, hard capsule, soft capsule, liquid (e.g., solution, suspension, milky lotion), drink, jelly, pudding, yogurt, candy, chewing gum, or the like. These can be produced by a known method. For example, indigestible polysaccharides, such as oligosaccharides or water-soluble dietary fiber, can be mixed with carriers, such as an excipient, binder, disintegrant, lubricant, or solvent, to produce a powder, granule, tablet, capsule, liquid, and the like by a method known in the field of food preparation or pharmaceutical preparation. In addition, they can also be produced by adding and mixing indigestible polysaccharides such as oligosaccharide or water-soluble dietary fiber to and with food and drink, such as water or a soft drink. Commercially available products, such as fructo-oligosaccharide "Meiorigo P granule" manufactured by Meiji Food Materia Co., Ltd., can also be used.

As described above, the food as described herein includes a food containing the above-mentioned (1) and (2) in one preparation, and a food combining the above-mentioned (1) and (2) formulated separately.

As the food combining (1) and (2) formulated separately, for example, a food is described combining (1) in the form of an enteric granule, enteric granulated substance, enteric tablet, enteric hard capsule, or enteric soft capsule containing amino acid or a salt thereof, and (2) in the form of a drink containing an indigestible polysaccharide, such as oligosaccharide or water-soluble dietary fiber.

(1) and (2) may be ingested simultaneously or at different times by the same route or different routes. Specifically, for example, an enteric capsule such as a hard capsule or soft capsule containing an amino acid or a salt thereof, enteric granule, enteric granulated substance, and the like may be ingested together with drink containing an indigestible polysaccharide such as an oligosaccharide or water-soluble dietary fiber. The ingestion amount of an amino acid or a salt thereof in the food for improving intestinal environment can be generally 0.1-50 g, 0.2-20 g, or 0.5-10 g, based on amino acid, per day for an adult (body weight 60 kg).

The ingestion amount of an indigestible polysaccharide such as an oligosaccharide or water-soluble dietary fiber in the food for improving intestinal environment can be generally 0.1-50 g, 0.2-20 g, or 0.5-10 g, per day for an adult (body weight 60 kg).

The food can be safely given to humans and animals other than human, such as mammals and birds such as domestic animals, poultry, experimental animals, and the like. When providing the food to animals other than human, it may be added to the animal's feed.

Further embodiments include a commercial package containing a food containing a combination of (1) an enteric composition containing an amino acid or a salt thereof and (2) an indigestible polysaccharide or a composition containing an indigestible polysaccharide, and written matter describing and explaining uses of the food for improving intestinal environment; a food with an indication that it is useful for improving intestinal environment, which contains a combination of (1) an enteric composition containing amino acid or a salt thereof and (2) indigestible polysaccharide or a composition containing indigestible polysaccharide; a food for enhancing the intestinal environment improving effect containing a combination of (1) an enteric composition containing an amino acid or a salt thereof and (2) an indigestible polysaccharide or a composition containing an indigestible polysaccharide; and a food for enhancing the intestinal environment improving effect of an indigestible polysaccharide or a composition containing an indigestible polysaccharide, which food is an enteric composition containing an amino acid or a salt thereof. The "enteric composition containing an amino acid or a salt thereof", "an indigestible polysaccharide or a composition containing indigestible polysaccharide", "intestinal environment improvement", "ingestion amount of amino acid or a salt thereof" and "ingestion amount of indigestible polysaccharides" are the same as exemplifications and definitions indicated for the above-described food for improving intestinal environment.

EXAMPLES

The present invention is explained in more detail by referring to the following non-limiting Experimental Examples, Examples, Comparative Examples, and Reference Examples.

Abbreviations mean the following:
Ala: L-alanine
Arg: L-arginine
Asn: L-asparagine
Cys: L-cysteine
Gln: L-glutamine
Glu: L-glutamic acid
Gly: glycine
His: L-histidine
Ile: L-isoleucine
Leu: L-leucine
Lys: L-lysine
Met: L-methionine
Phe: L-phenylalanine
Pro: L-proline
Ser: L-serine
Thr: L-threonine
Val: L-valine
FOS: fructo-oligosaccharide
GOS: galacto-oligosaccharide
PBS: phosphate buffered saline The PBS solutions for the Examples and Comparative Examples shown in Table 1-1 were prepared and used as media for a feces culture. PBS alone was used as a control. Fructo-oligosaccharide (FOS) manufactured by Wako Pure Chemical Industries, Ltd. (#064-02385) was used.

Thereafter, 10 ml of each solution was dispensed into glass vials and the glass vials were sterilized by autoclave, made anaerobic, and sealed with a butyl rubber stopper. The feces suspension was prepared by collecting about 10 g of feces from 3 healthy individuals (one man and two women) in their 20 s to 40 s and suspending same in 80 ml of anaerobic PBS. The feces suspension was added to each vial by 0.5 ml, placed in an incubator at 37° C., and anaerobically cultured for 4 days with tumble blending once per day. After completion of the culture, an intestinal bacterial pellet was obtained from the entire amount of the culture medium by centrifugation (8,000×g, 5 min). DNA was extracted from this pellet using ISOFECAL for BeadsBeat (manufactured by NIPPON GENE CO., LTD.), and quantitative PCR was performed using GeneAce SYBR qPCR Mix α (manufactured by NIPPON GENE CO., LTD.). Quantitative PCR was performed under the conditions of 45 cycles of 95° C. for 30 sec and 60° C. for 60 sec after 95° C. for 10 min. Primers for quantitative PCR used for detection bifidobacteria are as follows.

```
                              (SEQ ID NO: 1)
g-Bifid-F:    5'-CTCCTGGAAACGGGTGG-3'

(SEQ ID NO: 2)
g-Bifid-R:    5'-GGTGTTCTTCCCGATATCTACA-3'
```

TABLE 1-1

| | medium for feces culture |
|---|---|
| Example 1-1 | 0.1% Ala and 0.5% FOS-containing PBS solution |
| Example 1-2 | 0.5% Ala and 0.5% FOS-containing PBS solution |
| Example 1-3 | 1.0% Ala and 0.5% FOS-containing PBS solution |
| Example 2-1 | 0.1% Arg and 0.5% FOS-containing PBS solution |
| Example 2-2 | 0.5% Arg and 0.5% FOS-containing PBS solution |
| Example 2-3 | 1.0% Arg and 0.5% FOS-containing PBS solution |
| Example 3-1 | 0.1% Gln and 0.5% FOS-containing PBS solution |
| Example 3-2 | 0.5% Gln and 0.5% FOS-containing PBS solution |
| Example 3-3 | 1.0% Gln and 0.5% FOS-containing PBS solution |
| Example 4-1 | 0.1% Glu and 0.5% FOS-containing PBS solution |
| Example 4-2 | 0.5% Glu and 0.5% FOS-containing PBS solution |
| Example 4-3 | 1.0% Glu and 0.5% FOS-containing PBS solution |
| Example 5-1 | 0.1% Gly and 0.5% FOS-containing PBS solution |
| Example 5-2 | 0.5% Gly and 0.5% FOS-containing PBS solution |
| Example 5-3 | 1.0% Gly and 0.5% FOS-containing PBS solution |
| Example 6-1 | 0.1% Ile and 0.5% FOS-containing PBS solution |
| Example 6-2 | 0.5% Ile and 0.5% FOS-containing PBS solution |
| Example 6-3 | 1.0% Ile and 0.5% FOS-containing PBS solution |
| Example 7-1 | 0.1% Lys and 0.5% FOS-containing PBS solution |
| Example 7-2 | 0.5% Lys and 0.5% FOS-containing PBS solution |
| Example 7-3 | 1.0% Lys and 0.5% FOS-containing PBS solution |
| Example 8-1 | 0.1% Ser and 0.5% FOS-containing PBS solution |

TABLE 1-1-continued

| | medium for feces culture |
|---|---|
| Example 8-2 | 0.5% Ser and 0.5% FOS-containing PBS solution |
| Example 8-3 | 1.0% Ser and 0.5% FOS-containing PBS solution |
| Example 9-1 | 0.1% Val and 0.5% FOS-containing PBS solution |
| Example 9-2 | 0.5% Val and 0.5% FOS-containing PBS solution |
| Example 9-3 | 1.0% Val and 0.5% FOS-containing PBS solution |
| Example 10-1 | 0.1% Glu, 0.1% Lys and 0.5% FOS-containing PBS solution |
| Example 10-2 | 0.5% Glu, 0.5% Lys and 0.5% FOS-containing PBS solution |
| Example 10-3 | 1.0% Glu, 1.0% Lys and 0.5% FOS-containing PBS solution |
| Comparative Example 1 | 1.0% Ala-containing PBS solution |
| Comparative Example 2 | 1.0% Arg-containing PBS solution |
| Comparative Example 3 | 1.0% Gln-containing PBS solution |
| Comparative Example 4 | 1.0% Glu-containing PBS solution |
| Comparative Example 5 | 1.0% Gly-containing PBS solution |
| Comparative Example 6 | 1.0% Ile-containing PBS solution |
| Comparative Example 7 | 1.0% Lys-containing PBS solution |
| Comparative Example 8 | 1.0% Ser-containing PBS solution |
| Comparative Example 9 | 1.0% Val-containing PBS solution |
| Comparative Example 10 | 1.0% Glu and 1.0% Lys-containing PBS solution |
| Comparative Example 11 | 0.5% FOS-containing PBS solution |
| Reference Example 1 | PBS alone (control) |

Using the results obtained by quantitative PCR, the relative amount when the control is 1 was calculated, and the results were normalized with z-score.

The results are shown in FIG. 1-1. The data shows a mean of z-score±standard error (n=3).

As a result, proliferation of bifidobacteria was not observed when any amino acid was added alone. However, when Ala, Gln, Glu, Ile, Lys, and Val were respectively added together with 0.5% FOS, greater proliferation of bifidobacteria than that with FOS alone was observed. In addition, when Glu and Lys were mixed and added together with 0.5% FOS, greater proliferation of bifidobacteria than that with FOS alone was similarly observed.

Thus, a synergistic effect exceeding the additive effect was observed in the proliferation of bifidobacteria by combining an amino acid and an oligosaccharide.

Experimental Example 1-2: Addition Test of Amino Acid and Fructo-Oligosaccharide to Human Feces Suspension The PBS solutions for the Examples and Comparative Examples shown in Table 1-2 were prepared and used as media for a feces culture. PBS alone was used as a control. Feces culture and detection of bifidobacteria were performed according to methods similar to those in Experimental Example 1-1.

TABLE 1-2

| | medium for feces culture |
|---|---|
| Example 11-1 | 0.1% Asn and 0.5% FOS-containing PBS solution |
| Example 11-2 | 0.5% Asn and 0.5% FOS-containing PBS solution |

TABLE 1-2-continued

| | medium for feces culture |
|---|---|
| Example 11-3 | 1.0% Asn and 0.5% FOS-containing PBS solution |
| Example 12-1 | 0.1% Cys and 0.5% FOS-containing PBS solution |
| Example 12-2 | 0.5% Cys and 0.5% FOS-containing PBS solution |
| Example 12-3 | 1.0% Cys and 0.5% FOS-containing PBS solution |
| Example 13-1 | 0.1% His and 0.5% FOS-containing PBS solution |
| Example 13-2 | 0.5% His and 0.5% FOS-containing PBS solution |
| Example 13-3 | 1.0% His and 0.5% FOS-containing PBS solution |
| Example 14-1 | 0.1% Leu and 0.5% FOS-containing PBS solution |
| Example 14-2 | 0.5% Leu and 0.5% FOS-containing PBS solution |
| Example 14-3 | 1.0% Leu and 0.5% FOS-containing PBS solution |
| Example 15-1 | 0.1% Met and 0.5% FOS-containing PBS solution |
| Example 15-2 | 0.5% Met and 0.5% FOS-containing PBS solution |
| Example 15-3 | 1.0% Met and 0.5% FOS-containing PBS solution |
| Example 16-1 | 0.1% Phe and 0.5% FOS-containing PBS solution |
| Example 16-2 | 0.5% Phe and 0.5% FOS-containing PBS solution |
| Example 16-3 | 1.0% Phe and 0.5% FOS-containing PBS solution |
| Example 17-1 | 0.1% Pro and 0.5% FOS-containing PBS solution |
| Example 17-2 | 0.5% Pro and 0.5% FOS-containing PBS solution |
| Example 17-3 | 1.0% Pro and 0.5% FOS-containing PBS solution |
| Example 18-1 | 0.1% Thr and 0.5% FOS-containing PBS solution |
| Example 18-2 | 0.5% Thr and 0.5% FOS-containing PBS solution |
| Example 18-3 | 1.0% Thr and 0.5% FOS-containing PBS solution |
| Comparative Example 11 | 0.5% FOS-containing PBS solution |
| Comparative Example 12 | 1.0% Asn-containing PBS solution |
| Comparative Example 13 | 1.0% Cys-containing PBS solution |
| Comparative Example 14 | 1.0% His-containing PBS solution |
| Comparative Example 15 | 1.0% Leu-containing PBS solution |
| Comparative Example 16 | 1.0% Met-containing PBS solution |
| Comparative Example 17 | 1.0% Phe-containing PBS solution |
| Comparative Example 18 | 1.0% Pro-containing PBS solution |
| Comparative Example 19 | 1.0% Thr-containing PBS solution |
| Reference Example 1 | PBS alone (control) |

Using the results obtained by quantitative PCR, the relative amount when the control is 1 was calculated, and the results were normalized with z-score.

Figures 1, 2:
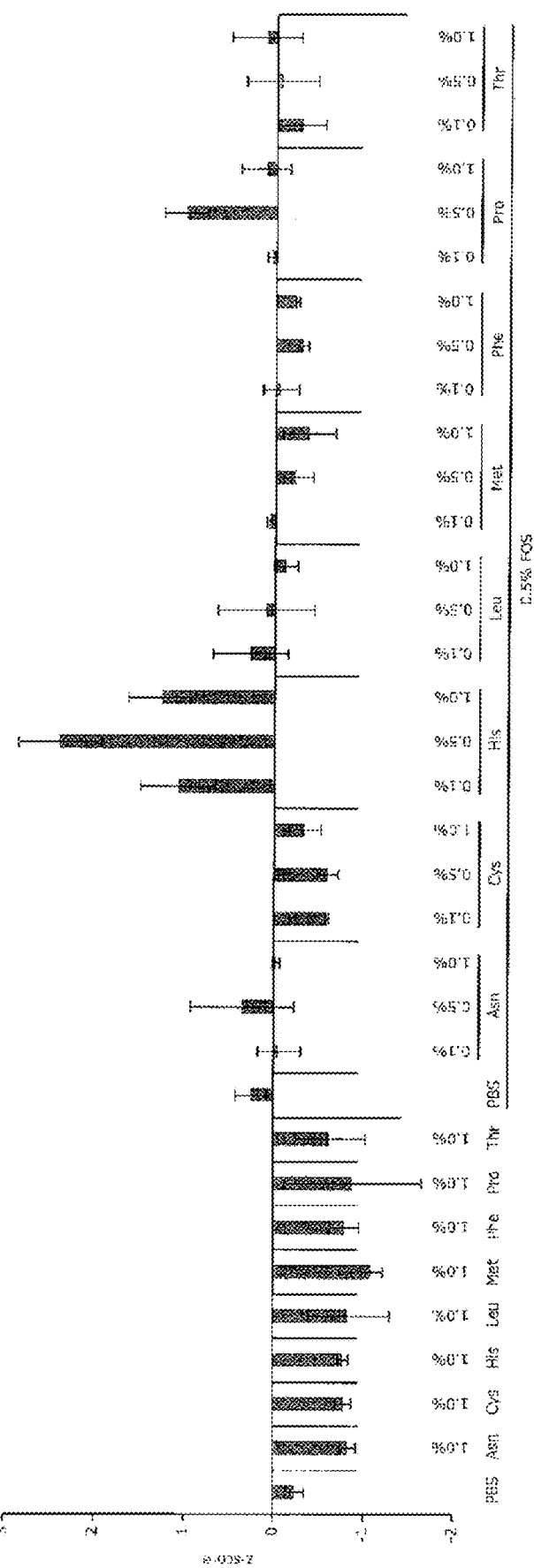
Figure 2:
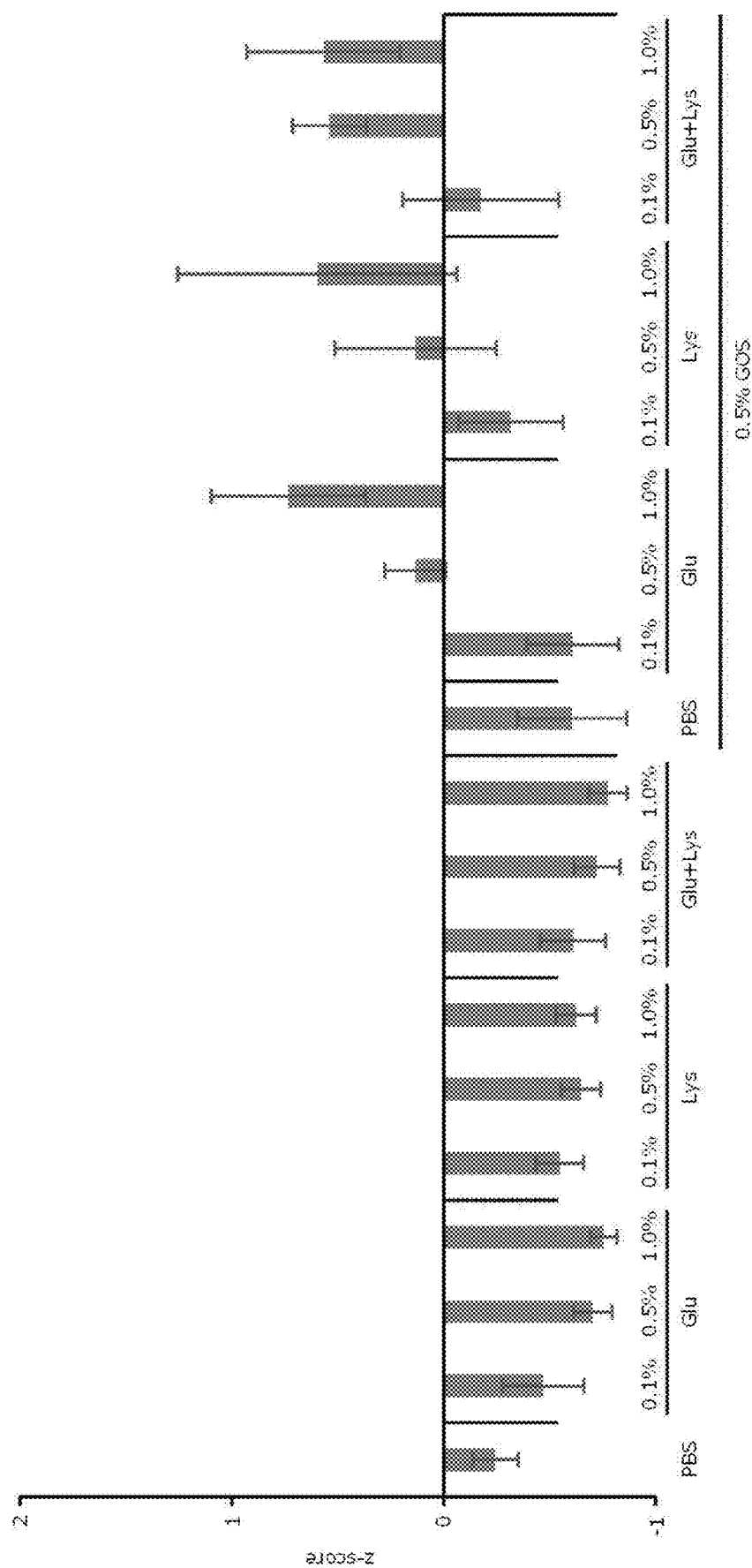

The results are shown in FIG. 1-2. The data shows a mean of z-score standard error (n=3).

As a result, proliferation of bifidobacteria was not observed when any amino acid was added alone. However, when His and Pro were respectively added together with 0.5% FOS, greater proliferation of bifidobacteria than that with FOS alone was observed.

Thus, a synergistic effect exceeding the additive effect was observed in the proliferation of bifidobacteria by combining an amino acid and an oligosaccharide.

Experimental Example 2: Addition Test of Amino Acid and Galacto-Oligosaccharide to Human Feces Suspension The PBS solutions for the Examples and Comparative Examples shown in Table 2 were prepared and used as media for feces culture. Feces culture and detection of bifidobacteria were performed according to methods similar to those in Experimental Example 1-1. Galacto-oligosaccharide (GOS) manufactured by Wako Pure Chemical Industries, Ltd. (#076-05945) was used.

TABLE 2

| | medium for feces culture |
|---|---|
| Example 19-1 | 0.1% Glu and 0.5% GOS-containing PBS solution |
| Example 19-2 | 0.5% Glu and 0.5% GOS-containing PBS solution |
| Example 19-3 | 1.0% Glu and 0.5% GOS-containing PBS solution |
| Example 20-1 | 0.1% Lys and 0.5% GOS-containing PBS solution |
| Example 20-2 | 0.5% Lys and 0.5% GOS-containing PBS solution |
| Example 20-3 | 1.0% Lys and 0.5% GOS-containing PBS solution |
| Example 21-1 | 0.1% Glu, 0.1% Lys and 0.5% GOS-containing PBS solution |
| Example 21-2 | 0.5% Glu, 0.5% Lys and 0.5% GOS-containing PBS solution |
| Example 21-3 | 1.0% Glu, 1.0% Lys and 0.5% GOS-containing PBS solution |
| Comparative Example 20-1 | 0.1% Glu-containing PBS solution |
| Comparative Example 20-2 | 0.5% Glu-containing PBS solution |
| Comparative Example 20-3 | 1.0% Glu-containing PBS solution |
| Comparative Example 21-1 | 0.1% Lys-containing PBS solution |
| Comparative Example 21-2 | 0.5% Lys-containing PBS solution |
| Comparative Example 21-3 | 1.0% Lys-containing PBS solution |
| Comparative Example 22-1 | 0.1% Glu and 0.1% Lys-containing PBS solution |
| Comparative Example 22-2 | 0.5% Glu and 0.5% Lys-containing PBS solution |
| Comparative Example 22-3 | 1.0% Glu and 1.0% Lys-containing PBS solution |
| Comparative Example 23 | 0.5% GOS-containing PBS solution |
| Reference Example 2 | PBS alone (control) |

Using the results obtained by quantitative PCR, the relative amount when the control is 1 was calculated, and the results were normalized with z-score.

The results are shown in FIG. 2. The data shows a mean of z-score±standard error (n=3).

As a result, proliferation of bifidobacteria was not observed when amino acid was added alone at any concentration. However, when Glu and Lys were respectively added together with 0.5% GOS, greater proliferation of bifidobacteria than that with GOS alone was observed. In addition, when Glu and Lys were mixed and added together with 0.5% GOS, greater proliferation of bifidobacteria than that with GOS alone was similarly observed.

Thus, a synergistic effect exceeding the additive effect was observed in the proliferation of bifidobacteria by combining an amino acid and an oligosaccharide irrespective of the type thereof.

Experimental Example 3: Administration test of enteric Lys and FOS to pigs

Six 2 to 3 months-old male pigs (HI-COOP SPF pig LWD) were purchased from ZEN-NOH, divided into 2 test groups each containing 3 pigs such that the average body weight was uniform, and kept for 4 weeks at 3 pigs/pen. In each test group, 400 g/head of pig MIRAI CEX (ZEN-NOH) was fed twice per day. In each test group, the test substance was administered by the dosage and method shown in Table 3. A lysine preparation "AjiPro-L" for dairy cows manufactured by Ajinomoto Co., Inc. (lysine hydrochloride content is 40% or more) was used as Enteric Lys, and fructo-oligosaccharide "Mayoligo P granule" manufactured by Meiji Food Materia Co., Ltd. (FOS content is 95% or more) was used as FOS. After 4 weeks from the start of administration, the cecum was collected, and bifidobacteria in the cecal contents were examined by quantitative PCR in the same manner as in Experimental Examples 1-1, 1-2 and 2. The concentration of Lys in the cecum contents was measured using 6470 Triple Quad LC/MS/MS system manufactured by Agilent and Intrada Amino Acid column manufactured by Imtakt.

TABLE 3

| | dosage and administration method of test substance |
|---|---|
| Example 22 | FOS: Meiorigo P granule (10 g) was mixed with each meal Enteric Lys: Oral administration of 2 cellulose capsules after each meal, each capsule encapsulating 6 g of AjiPro-L |
| Comparative Example 24 | FOS: Meiorigo P granule (10 g) was mixed with each meal placebo: Oral administration of 2 empty cellulose capsules after each meal |

Figure 3:
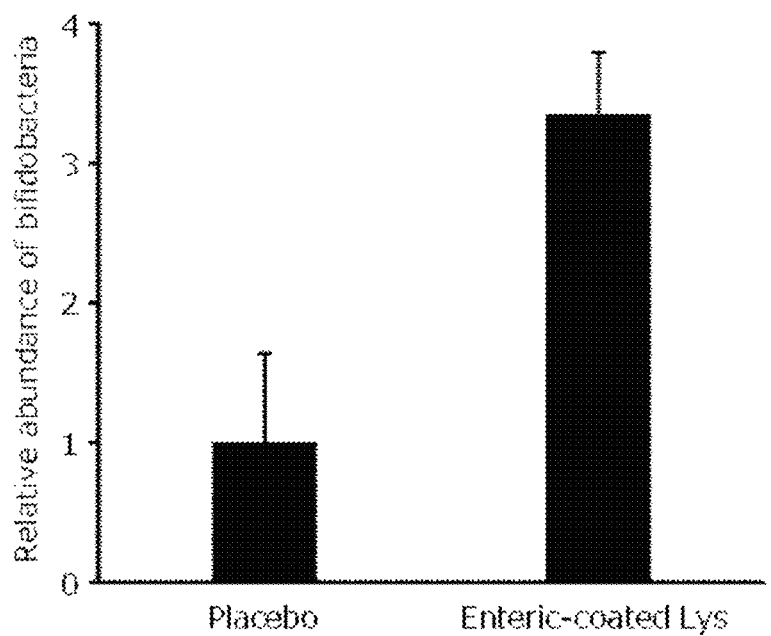
FIG. 3 shows the results of relative amounts of cecal bifidobacteria in Experimental Example 3.

The results obtained by quantitative PCR are shown as relative amounts when Comparative Example 24 (placebo) is 1. The results of the relative amount of bifidobacteria in the cecum are shown in FIG. 3 (mean±standard deviation, n=3). As a result, pig intestinal bifidobacteria proliferation is about 3 times higher on average when the combination of enteric Lys and FOS was ingested than by the ingestion of FOS alone.

Figure 4:
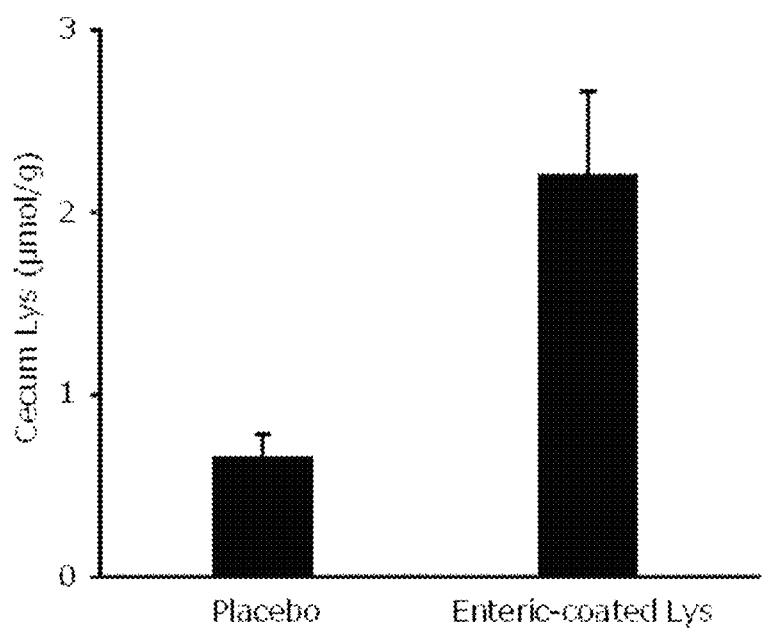
FIG. 4 shows the results of cecal lysine concentration in Experimental Example 3.

In addition, the results of the concentration of Lys in the cecum at that time are shown in FIG. 4 (mean±standard deviation, n=3). As a result, it was confirmed that the concentration of Lys in the cecum increased in the enteric Lys ingestion group.

Thus, a synergistic effect with fructo-oligosaccharide was observed by increasing the concentration of Lys in the lower gastrointestinal tract by the ingestion of enteric Lys.

We claim:

1. A food for improving an intestinal environment in a subject comprising:
   (1) an enteric composition comprising an amino acid or a salt thereof in an amount of 0.1 to 50 g/60 kg body weight of the subject, and
   (2) an indigestible polysaccharide or a composition comprising an indigestible polysaccharide, wherein the indigestible polysaccharide is in an amount of 0.1 to 50 g/60 kg body weight of the subject;
   wherein a synergistic effect exceeding an additive effect in the proliferation of Bifidobacteria is observed after combining (1) and (2).

2. The food according to claim 1, wherein the indigestible polysaccharide is an oligosaccharide.

3. The food according to claim 1, wherein the amino acid is selected from the group consisting of alanine, glutamine, glutamic acid, isoleucine, histidine, lysine, proline, valine, and combinations thereof.

4. The food according to claim 1, wherein the amino acid is selected from the group consisting of glutamic acid, lysine, and a combination thereof.

5. The food according to claim 1, wherein the form of the enteric composition is selected from the group consisting of a granule, a granulated substance, a tablet, a hard capsule, and a soft capsule.

6. A method for improving an intestinal environment in a human comprising ingestion by the human of an effective amount of a food comprising:
   (1) an enteric composition comprising an amino acid or a salt thereof in an amount of 0.1 to 50 g/60 kg body weight of the human, and
   (2) an indigestible polysaccharide or a composition comprising an indigestible polysaccharide, wherein the indigestible polysaccharide is in an amount of 0.1 to 50 g/60 kg body weight of the human;
   wherein a synergistic effect exceeding an additive effect in the proliferation of Bifidobacteria is observed after combining (1) and (2).

7. A method of producing a food for improving the intestinal environment in a subject comprising combining (1) an enteric composition comprising an amino acid or a salt thereof in an amount of 0.1 to 50 g/60 kg body weight of the subject, and (2) an indigestible polysaccharide or a composition comprising an indigestible polysaccharide, wherein the indigestible polysaccharide is in an amount of 0.1 to 50 g/60 kg body weight of the subject;
   wherein a synergistic effect exceeding an additive effect in the proliferation of Bifidobacteria is observed after combining (1) and (2).

* * * * *